(12) United States Patent
Draper et al.

(10) Patent No.: US 10,173,005 B2
(45) Date of Patent: Jan. 8, 2019

(54) DRUG DELIVERY DEVICE

(71) Applicant: Sanofi-Aventis Deutschland GmbH, Frankfurt am Main (DE)

(72) Inventors: Paul Richard Draper, Worcestershire (GB); George Cave, Warwickshire (GB); Joseph Butler, Warwickshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 381 days.

(21) Appl. No.: 14/762,068

(22) PCT Filed: Jan. 27, 2014

(86) PCT No.: PCT/EP2014/051472
§ 371 (c)(1),
(2) Date: Jul. 20, 2015

(87) PCT Pub. No.: WO2014/118109
PCT Pub. Date: Aug. 7, 2014

(65) Prior Publication Data
US 2015/0320932 A1 Nov. 12, 2015

(30) Foreign Application Priority Data

Jan. 29, 2013 (EP) .................................... 13153139

(51) Int. Cl.
*A61M 5/172* (2006.01)
*A61M 5/145* (2006.01)
(Continued)

(52) U.S. Cl.
CPC .......... *A61M 5/172* (2013.01); *A61M 5/1454* (2013.01); *A61M 5/20* (2013.01);
(Continued)

(58) Field of Classification Search
CPC ...... A61M 2005/2073; A61M 2205/50; A61M 2205/502; A61M 2205/8237;
(Continued)

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| EP | 0937471 A2 | 8/1999 |
| EP | 0937476 A2 | 8/1999 |

(Continued)

*Primary Examiner* — Bhisma Mehta
*Assistant Examiner* — Brandy S Lee
(74) *Attorney, Agent, or Firm* — Fish & Richardson P.C.

(57) ABSTRACT

The invention relates to a drug delivery device for administering a drug, comprising: a body adapted to retain a cartridge containing a drug, at least one electrical unit (EU) and a port for electrically contacting the electrical unit (EU), an adapter for attaching an injection needle to the drug delivery device, a safety mechanism (S1 to S6) arranged to prevent access to the port while an injection needle is in fluid communication with the cartridge and arranged to prevent establishing a fluid communication between an injection needle and the cartridge while the port is accessible.

15 Claims, 8 Drawing Sheets

(51) Int. Cl.
  *A61M 5/32* (2006.01)
  *A61M 5/24* (2006.01)
  *A61M 5/34* (2006.01)
  *A61M 5/20* (2006.01)

(52) U.S. Cl.
  CPC ............ *A61M 5/24* (2013.01); *A61M 5/3293* (2013.01); *A61M 5/34* (2013.01); *A61M 5/3202* (2013.01); *A61M 5/345* (2013.01); *A61M 5/347* (2013.01); *A61M 2005/2073* (2013.01); *A61M 2205/50* (2013.01); *A61M 2205/502* (2013.01); *A61M 2205/8237* (2013.01); *A61M 2205/8262* (2013.01)

(58) Field of Classification Search
  CPC ........ A61M 2205/8262; A61M 5/1454; A61M 5/172; A61M 5/20; A61M 5/24; A61M 5/3202; A61M 5/3293; A61M 5/34; A61M 5/345; A61M 5/347
  See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2009/0275916 A1 | 11/2009 | Harms et al. | |
| 2011/0201999 A1 | 8/2011 | Cronenberg et al. | |
| 2013/0079708 A1* | 3/2013 | Wimpenny | A61M 5/002 604/65 |

FOREIGN PATENT DOCUMENTS

| | | |
|---|---|---|
| WO | 9938554 A1 | 8/1999 |
| WO | 0110484 A1 | 2/2001 |
| WO | 2008045203 A1 | 4/2008 |
| WO | 2009113060 A2 | 9/2009 |
| WO | 2011117404 A2 | 9/2011 |

\* cited by examiner

DRUG DELIVERY DEVICE

CROSS REFERENCE TO RELATED APPLICATIONS

The present application is a U.S. National Phase Application pursuant to 35 U.S.C. § 371 of International Application No. PCT/EP2014/051472 filed Jan. 27, 2014, which claims priority to European Patent Application No. 13153139.4 filed Jan. 29, 2013. The entire disclosure contents of these applications are herewith incorporated by reference into the present application.

FIELD OF INVENTION

The invention relates to a drug delivery device.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring. In other devices this is achieved by an electromechanical drive. Devices with electromechanical and/or electronic components may comprise a port which may serve for wired communication with another device for data transfer or for charging.

SUMMARY

It is an object of the present invention to provide an improved drug delivery device.

The object is achieved by a drug delivery device according to claim 1.

Preferred embodiments of the invention are given in the dependent claims.

According to the invention a drug delivery device for administering a drug comprises:
- a body adapted to retain a cartridge containing a drug,
- at least one electrical unit and a port for electrically contacting the electrical unit,
- an adapter for attaching an injection needle to the drug delivery device,
- a safety mechanism arranged to prevent access to the port whilst an injection needle is in fluid communication with the cartridge and arranged to prevent establishing a fluid communication between an injection needle and the cartridge whilst the port is accessible.

The port, e.g. a USB port, may serve for wired communication with another device for data transfer or charging. The safety mechanism avoids the risk that the user may inadvertently leave the drug delivery device connected via a cable whilst attempting to inject. In this case there may exist a potential conductive path from the externally connected device, through the cable, the port and the electronics of the drug delivery device to the patient via the conductive metal injection needle. In case of a current overload on the port or a leaking cartridge which creates a short-circuit within the drug delivery device, the patient would be subjected to an electric shock. An electric shock may occur either if both the patient and the external device connected to the port are grounded or if the patient touches the port whilst they were injecting regardless of whether a cable is connected to the port or not. Similarly, the port may be adapted to interface with a blood glucose strip for measuring a user's blood glucose value. The port will thus also feature electronic contacts. Consequently there is a similar associated risk. The safety mechanism according to the invention prevents this risk.

The above risk is addressed by providing a safety mechanism arranged to prevent access to the port whilst an injection needle is in fluid communication with the cartridge and arranged to prevent establishing a fluid communication between an injection needle and the cartridge whilst the port is accessible.

Other options would be to have the safety mechanism disable the dosing operation of the drug delivery device when the user can access the port. This may be achieved by performing an operation which disables a delivery mechanism of the drug delivery device or by preventing the user from accessing a button or soft button on a human-machine interface for operating the drug delivery device.

In an exemplary embodiment the body comprises an inner body slidable within an outer body between a proximal position and a distal position, wherein the adapter is arranged on the inner body, and wherein the cartridge and the port are fixed to the outer body. A first opening is provided in the outer body for accessing the port, wherein a sliding cover is fixed to the inner body such that the cover closes the first opening when the inner body is in the proximal position and that the cover exposes the first opening when the inner body is in the distal position.

A proximal end of the needle may pierce a septum on the cartridge for establishing a fluid communication between the needle and a cavity within the cartridge when the inner body is in the proximal position within the outer body. The adapter in this embodiment is always accessible to the user, and consequently they can always fit a needle to the drug delivery device. However, if the inner body is moved in the distal position the adapter is moved away from the cartridge thus pulling the proximal tip of the needle out of the septum and interrupting the fluid communication between the needle and the cartridge. Hence, the potential conductive path is interrupted as the port is accessible thus preventing electric shock hazard.

In an exemplary embodiment the body comprises an inner body slidable within an outer body between a proximal position and a distal position, wherein the adapter is arranged on the inner body and extendible through a second opening in the outer body. The cartridge and the port are fixed to the inner body, wherein a first opening is provided in the inner body for accessing the port, wherein a sliding cover is fixed to the outer body such that the cover closes the first opening when the inner body is in the distal position and that the cover exposes the first opening when the inner body is in the proximal position. This prevents access to the adapter for attaching a needle if the port is accessible.

In an exemplary embodiment the port and the adapter are located on a distal end of the drug delivery device and accessible through respective first and second openings in a distal face of the body, wherein a sliding cover is movable in the distal face such that it either covers the first opening or the second opening.

In an exemplary embodiment a cartridge holder is arranged within the body for retaining the cartridge, wherein the adapter is arranged on the cartridge holder.

In an exemplary embodiment the cartridge and/or the cartridge holder is/are slidably arranged within the body between a proximal position, in which the adapter is inside the body, and a distal position, in which the adapter extends beyond the distal face. This improves access to the adapter when the cartridge or cartridge holder is advanced to extend the adapter and makes access more difficult when the cartridge or cartridge holder is retracted to hide the adapter.

In an exemplary embodiment a diameter of the second opening is smaller than a diameter of a needle hub of the needle for attaching the needle to the adapter. This prevents retraction of the adapter into the body while the needle is attached thereby also preventing movement of the sliding cover such that the port cannot be exposed while a needle is attached.

In an exemplary embodiment a drive is arranged for moving the cartridge and/or the cartridge holder towards the distal position. The adapter may thus automatically be advanced when the cover is moved to expose the second opening.

In an exemplary embodiment the drive comprises at least one spring. In other embodiments the drive may comprise electromechanical actors or a mechanical link connecting the motion of the cover to the motion of the cartridge and/or cartridge holder such that the cartridge is advanced when the cover is moved to close the first opening and retracted when the cover is moved to close the second opening.

In order to facilitate operation a slide handle may be coupled to the cover.

In an exemplary embodiment the port is located within the body, wherein a cartridge hub is adapted to close a distal end of the body thereby covering the port, wherein the adapter is arranged on the cartridge hub. The cartridge hub may have the shape of a cap which may be attached to the body by a friction fit, snap fit, screw thread, bayonet fit, etc.

In an exemplary embodiment of a hinge is provided on the body for hinging the cartridge hub to the body such that the cartridge hub is rotatable about the hinge for opening or closing the distal end of the body. In an exemplary embodiment the adapter comprises a threaded area for attaching a threaded needle. Instead of the threaded area the adapter may comprise other means for attaching the needle such as a bayonet fit, a cone or a Luer-lock.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
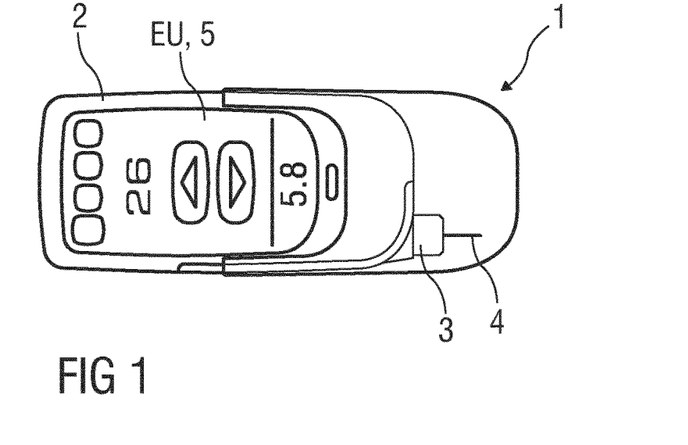
FIG. 1 is a schematic view of a first exemplary embodiment of an electromechanical drug delivery device.

FIG. 1 is a schematic view of a first exemplary embodiment of an electromechanical drug delivery device 1 for administering a drug. The drug delivery device 1 comprises a body 2 adapted to receive a drug cartridge 3 or syringe. A hypodermic needle 4 may be attached to the cartridge 3. The drug delivery device 1 further comprises an electrical unit EU such as a human-machine-interface 5 for communicating information to a user and for allowing the user to operate the drug delivery device 1. Furthermore, the drug delivery device 1 may comprise an electromechanical drive (not illustrated) for inserting the needle 4 into an injection site, e.g. a patient's skin and/or dispensing drug from the cartridge 3 through the needle 4 and/or retracting the needle 4 post-injection.

The needle 4 may be attached and removed by the user thus allowing it to be used for a single delivery of the drug. After delivery the needle is removed, discarded and replaced by a new one, if applicable.

Figure 2:
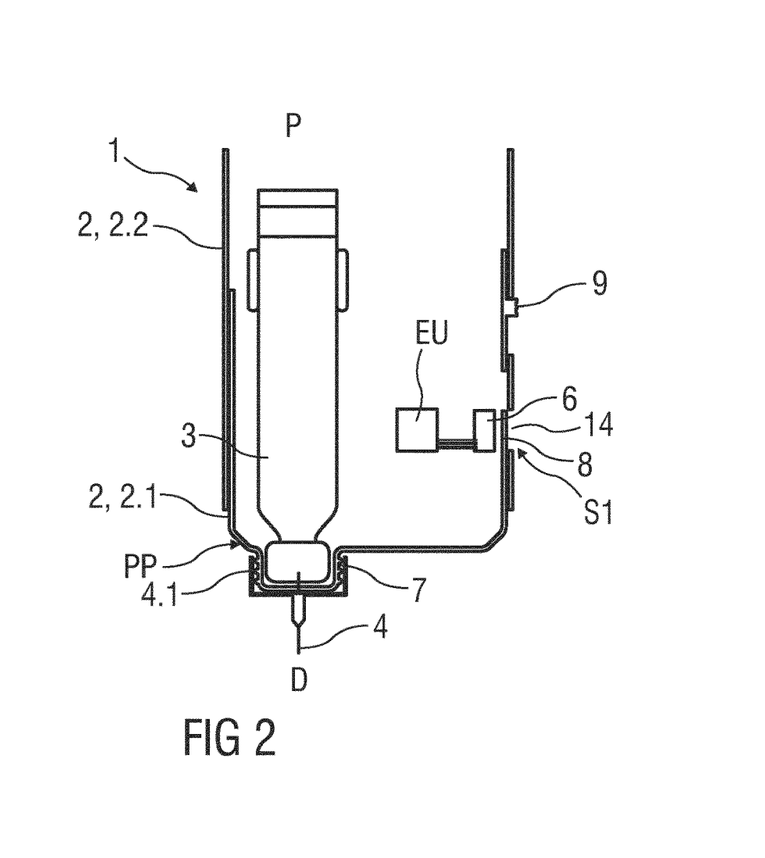
FIG. 2 is a schematic longitudinal section of the first embodiment of the drug delivery device with a needle in fluid communication with a cartridge while a port is covered.

FIG. 2 is a schematic longitudinal section of the drug delivery device 1.

The drug delivery device 1 comprises a port 6 which may serve for wired communication with another device for data transfer or charging. There is an associated risk with this feature that the user may inadvertently leave the drug delivery device 1 connected via a cable whilst attempting to inject. Whilst a control unit of the drug delivery device 1 may run software including checks to prevent the delivery of the drug in this situation, there will still exist a potential conductive path from the externally connected device, through the cable, the port 6 and the electronics of the drug delivery device 1 to the patient via the conductive metal needle 4. It is thus possible that, for instance, a current overload on the port 6 or a leaking cartridge 3 which creates a short-circuit within the drug delivery device 1, could deliver an electric shock to the patient. This may occur either if both the patient and the external device connected to the port 6 are grounded or if the patient touches the port 6 whilst they were injecting regardless of whether a cable is connected to the port 6 or not.

Similarly, the port 6 may be adapted to interface with a blood glucose strip for measuring a user's blood glucose value. The port 6 will thus also feature electronic contacts. Consequently there is a similar associated risk.

The above risk is addressed by providing a safety mechanism to disable the dosing operation of the drug delivery device 1 when the user can access the port 6. This is achieved by performing an operation which disables a delivery mechanism of the drug delivery device 1 or by preventing the user from accessing an adapter 7 such as a threaded area 7 of the drug delivery device adapted to connect to the needle 4 or from accessing a button or soft button on the human-machine interface 5.

Figure 3:
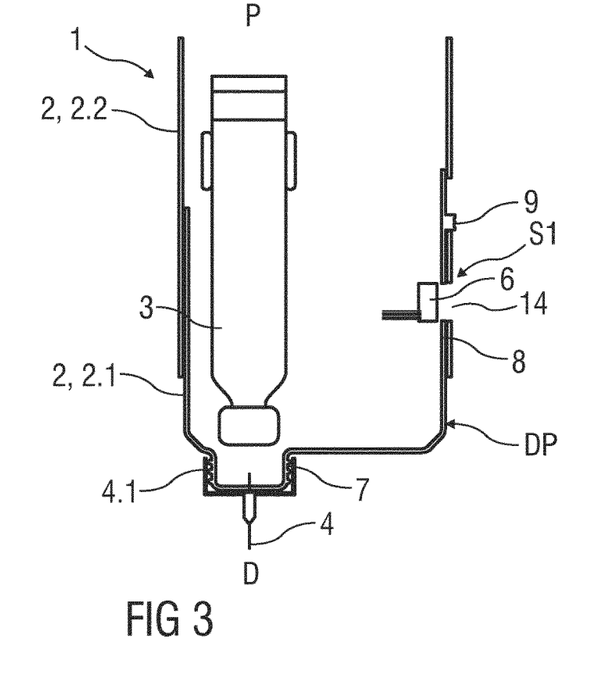
FIG. 3 is a schematic longitudinal section of the first embodiment of the drug delivery device, wherein the fluid communication between the needle and the cartridge is interrupted while the port is exposed.

The drug delivery device 1 in FIG. 2 comprises an inner body 2.1 and an outer body 2.2. The threaded area 7 of the drug delivery device 1 is attached to the inner body 2.1, whilst the cartridge 3 is fixed to the outer body 2.2 such that the inner body 2.1 can slide within the outer body 2.2 for moving the threaded area 7 relative to the cartridge 3 between a proximal position PP as illustrated in FIG. 2 and a distal position as illustrated in FIG. 3. A proximal end of the needle 4 may pierce a septum on the cartridge 3 for establishing a fluid communication between the needle 4 and a cavity within the cartridge 3 when the inner body 2.1 is in the proximal position within the outer body 2.2.

The threaded area 7 in this embodiment is always accessible to the user, and consequently they can always fit a threaded needle 4 to the drug delivery device 1 assuming that other blocking components, for instance a cap, are not present. In FIG. 2 the port 6, which is fixed to the outer body 2.2 and accessible through a first opening 14 in the outer body 2.2, is shielded by a sliding cover 8 being part of the safety mechanism 51. The user can gain access to the port 6 by a handle 9 which slides the sliding cover 8 open as in FIG. 3. The sliding cover 8 and the handle 9 are both parts of the inner body 2.1, such that when the user slides the cover 8 open, the inner body 2.1 is translated axially away from the cartridge 3 into a distal position, disconnecting the needle 4 from the cartridge 3 and interrupting their fluid communication. Thus, the user is unable to access the port 6 whilst a needle 4 is connected to the cartridge 3, thus mitigating the risk described above.

Figure 4:
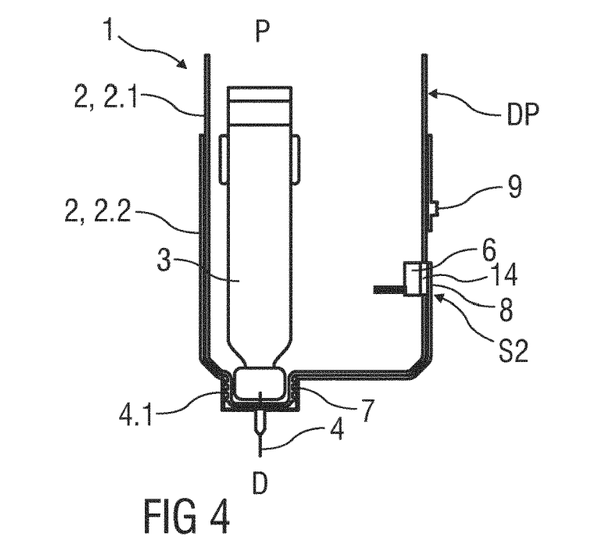
FIG. 4 is a second exemplary embodiment of the drug delivery device with a modified arrangement of the inner body and outer body, wherein the inner body is in a distal position.

FIG. 4 shows a second exemplary embodiment with a modified arrangement of the inner body 2.1 and outer body 2.2. In this embodiment, the safety mechanism S2 comprises the sliding cover 8 and the handle 9 attached to the outer body 2.2 which wraps around the inner body 2.1. In the embodiment of FIG. 4 the port 6 is fixed to the inner body 2.1. The sliding cover 8 is closed over the port 6 for preventing the user from accessing the port 6 when the inner body 2.1 is in the distal position DP with respect to the outer body 2.2. A needle 4 can only be attached to the threaded area 7 in the distal position DP of the inner body 2.1.

If the user wishes to access the port 6, they can actuate the outer body 2.2 by means of the handle 9. This pushes a distal end of the outer body 2.2 over the threaded area 7 of the inner body 2.1 if no needle 4 is present such that the inner body 2.1 arrives in the proximal position PP within the outer body 2.2 as in FIG. 5. If the needle 4 is attached to the threaded area 7 a collision between a needle hub 4.1 and the outer body 2.2 prevents translation of the outer body 2.2 with respect to the inner body 2.1. This may be achieved by the needle hub 4.1 having a greater diameter than a second opening 15 in the outer body 2.2 which the threaded area 7 may extend through for attaching the needle 4.

Figure 5:
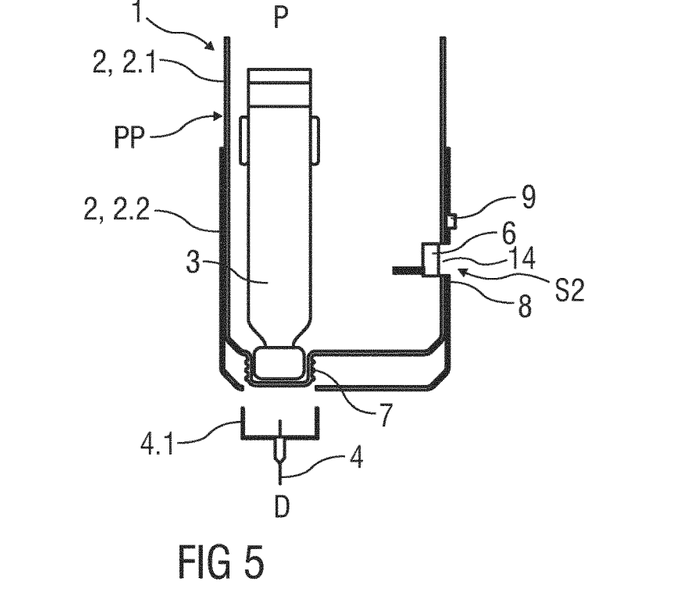
FIG. 5 is the second exemplary embodiment of the drug delivery device, wherein the inner body is in a proximal position.

When the needle 4 has been removed from the threaded area 7, the outer body 2.2 is free to slide relative to the inner body 2.1, and the user can gain access to the port 6 but is prevented from accessing the threaded area 7 as illustrated in FIG. 5.

Figure 6:
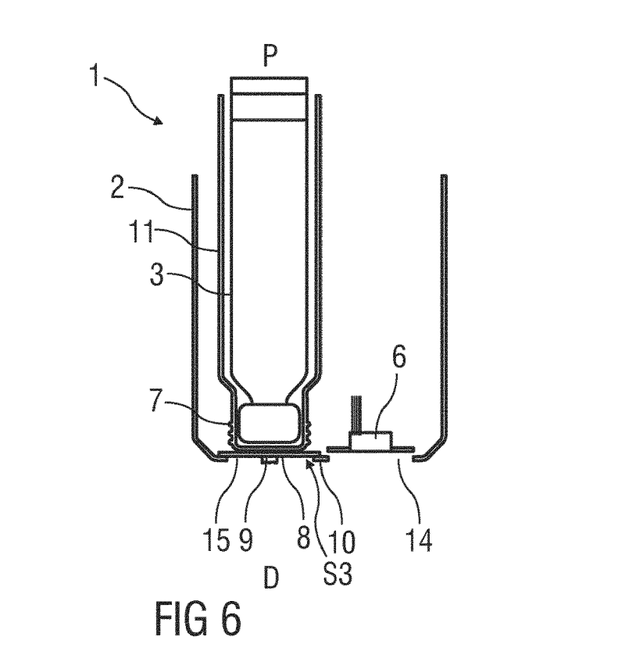
FIG. 6 is a schematic longitudinal section of a third exemplary embodiment of the drug delivery device with the port exposed.
Figure 8:
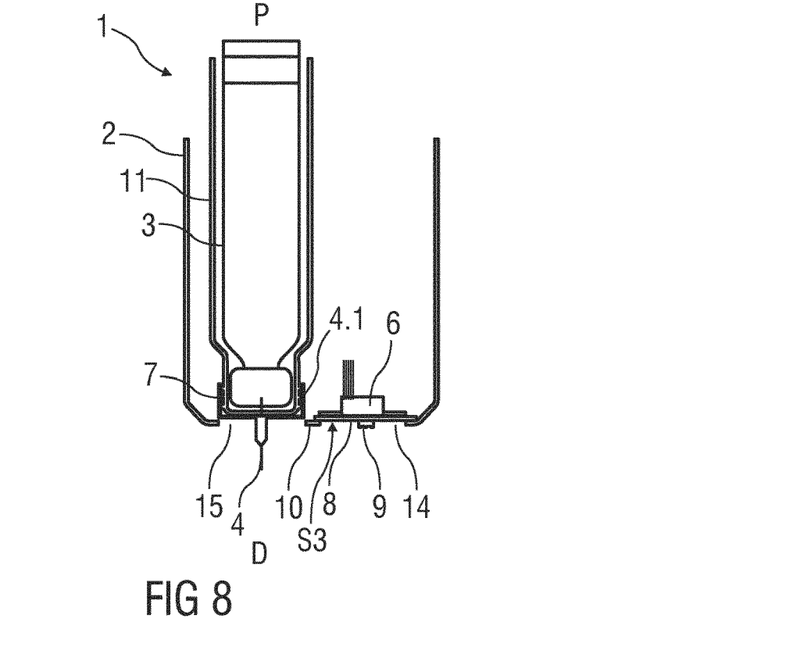
FIG. 8 is a schematic longitudinal section of the third exemplary embodiment of the drug delivery device with the port covered and a needle fit to the adapter.

FIG. 6 is a schematic longitudinal section of a third exemplary embodiment of the drug delivery device 1. In this embodiment the body 2 does not have to comprise two parts slidable relative to each other. Instead, the port 6 and the threaded area 7 are both located on the distal end of the drug delivery device 1 and accessible through the first opening 14 and the second opening 15 respectively. The threaded area 7 may be arranged on a cartridge holder 11 for retaining the cartridge 3. The safety mechanism S3 comprises a sliding cover 8 movable in a distal face 10 of the body 2 such that it either covers the threaded area 7 and exposes the port 6 or that it covers the port 6 and exposes the threaded area 7. If the user wishes to access the port 6, the cover 8 is located over the threaded area 7, blocking access to it as in FIG. 5. The user can use the slide handle 9 to move the cover 8 to block access to the port 6 and in doing so gain access to the threaded area 7 as illustrated in FIG. 6. This enables the user to fit a needle 4 to the drug delivery device 1 as illustrated in FIG. 8.

Figure 7:
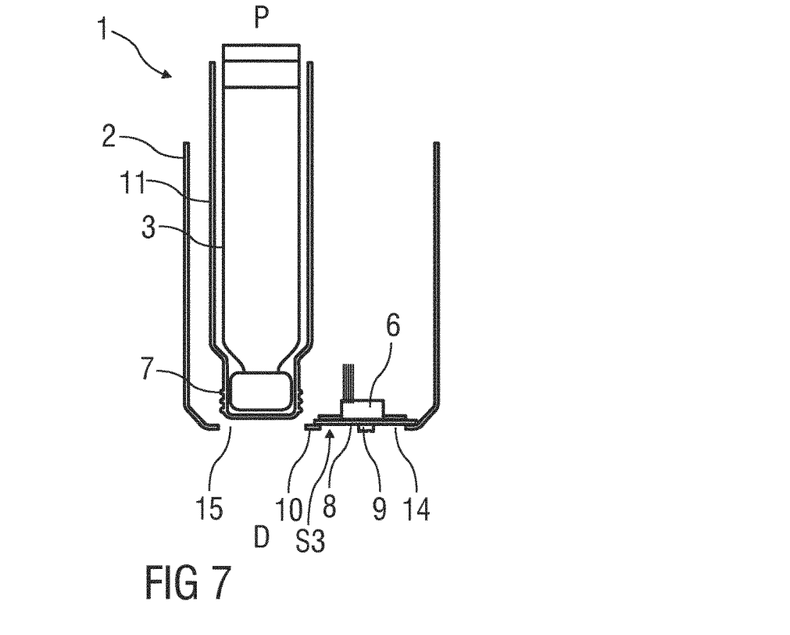
FIG. 7 is a schematic longitudinal section of the third exemplary embodiment of the drug delivery device with the port covered and an adapter exposed.
Figure 9:
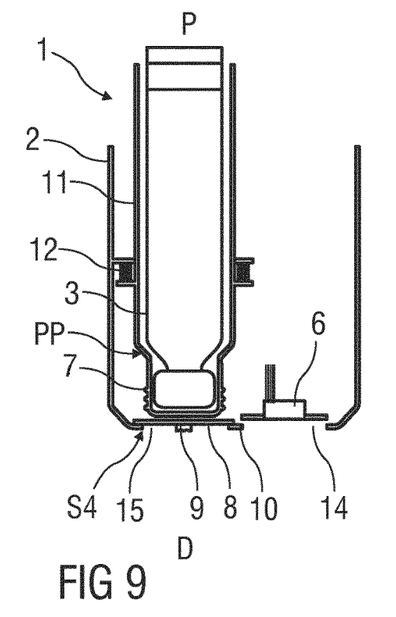
FIG. 9 is a schematic longitudinal section of a fourth exemplary embodiment of the drug delivery device with the port exposed.
Figure 10:
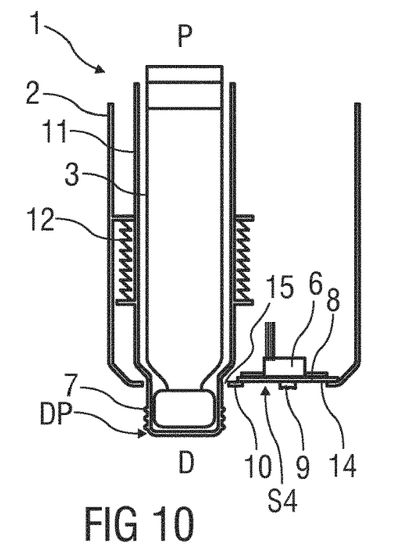
FIG. 10 is a schematic longitudinal section of the fourth exemplary embodiment of the drug delivery device with the port covered and the adapter advanced.
Figure 11:
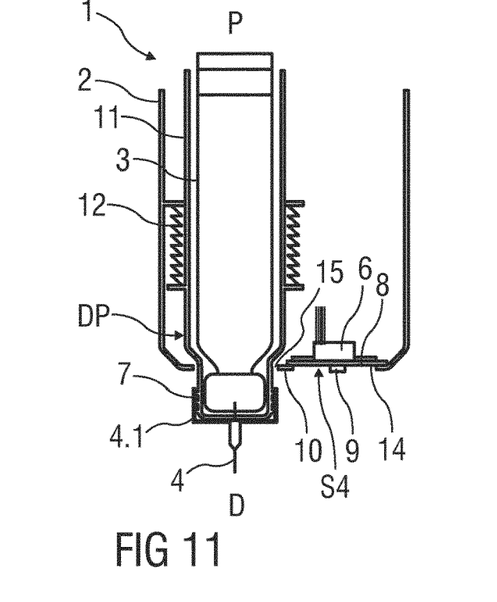
FIG. 11 is a schematic longitudinal section of the fourth exemplary embodiment of the drug delivery device with the port covered and a needle fit to the adapter.

FIG. 9 is a schematic longitudinal section of a fourth exemplary embodiment of the drug delivery device 1. In this embodiment the threaded area 7 of the cartridge holder 11 may be extended beyond the distal end of the drug delivery device 1. The embodiment shown in FIG. 9 is a modification of the embodiment of FIGS. 6 to 8, in which the cartridge 3 is restrained within a cartridge holder 11 which is slidably arranged within the body 2 between a proximal position PP (FIG. 9) and a distal position DP (FIGS. 10, 11) and sprung via springs 12 to the body 2. A sliding cover 8 is movable in a distal face 10 of the body 2 such that it either covers the threaded area 7 and exposes the port 6 or that it covers the port 6 and exposes the threaded area 7. If the user wishes to access the port 6, the cover 8 is located over the threaded area 7, blocking access to it as in FIG. 9. The user can use the slide handle 9 to move the cover 8 to block access to the port 6 and in doing so the cartridge holder 11 is released to move in the distal direction D with respect to the body 2 driven by the springs 12 thus giving the user access to the threaded area 7 as illustrated in FIG. 10. This enables the user to fit a needle 4 to the drug delivery device 1 as illustrated in FIG. 11. To return the drug delivery device 1 to the initial state of FIG. 9, the user can remove the needle 4 and push the cartridge holder 11 into the body 2 either directly or through the use of another sliding handle (not shown) on the side of the body 2, and then move the cover 8 to prevent access to the threaded area 7 but allow access to the port 6.

In an alternative embodiment, an electronic contact, such as a switch or micro-switch is used to detect movement of the cover 8 by the user. An electronic signal is generated that triggers an electro mechanic drive to drive the cartridge holder 11 in the distal direction D with respect to the body 2, thus replacing springs 12. Another switch or sensor that detects abutment of the shoulders of the cartridge holder 11 against the body 2 can be used to stop the electro mechanic drive. Similarly, the electro mechanic drive can retract the cartridge holder 11 when it is detected that the cover 8 is moved again, or when another button is pressed.

The fourth embodiment could also be extended to connect the motion of the cover 8 to the motion of the cartridge holder 11. This would remove the need for a spring 12 to move the cartridge holder 11 out of the body 2, and would avoid the user having to manually push the cartridge holder 11 into the body 2 prior to moving the cover 8.

Figure 12:
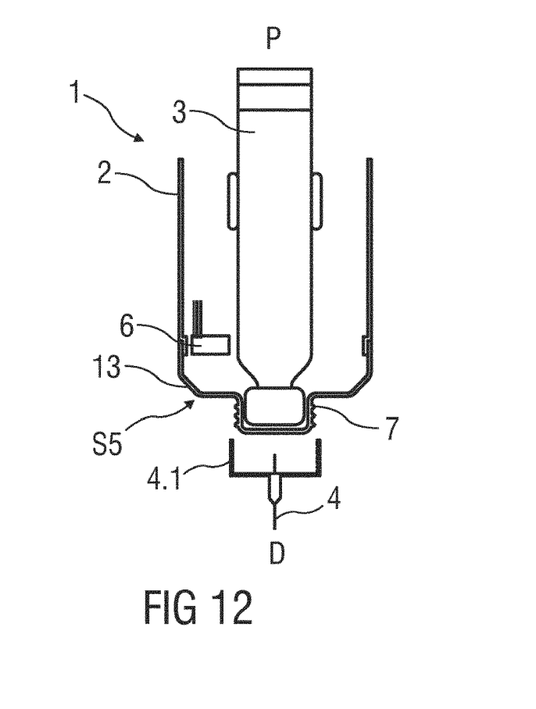
FIG. 12 is a schematic longitudinal section of a fifth exemplary embodiment of the drug delivery device, wherein the port is located within the body and a cartridge hub is arranged for closing the body.
Figure 13:
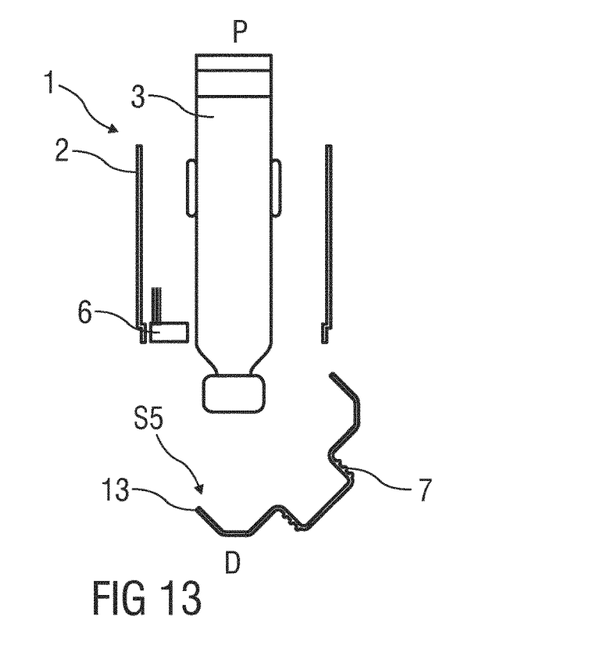
FIG. 13 is a schematic longitudinal section of the fifth exemplary embodiment of the drug delivery device, wherein the cartridge hub is removed.

A fifth exemplary embodiment is illustrated in FIG. 12. The port 6 is located within the body 2 next to the cartridge 3 behind a cartridge hub 13 comprised in the safety mechanism S5. The cartridge hub 13 comprises the threaded area 7, to which the needle 4 can be attached. The cartridge hub 13 is adapted to be attached to the body 2 as in FIG. 12. In this state the port 6 is hidden behind the cartridge hub 13 and cannot be accessed by the user. In order to access the port 6 the needle 4 is removed from the drug delivery device 1, and then the cartridge hub 13 is detached from the body 2 as illustrated in FIG. 13. This allows access to the port 6 for the user, but prevents them from fitting a needle 4 to the cartridge 3 as the cartridge 3 is not threaded. The user could likewise remove the cartridge hub 13 from the body 2 while the needle 4 is still attached to the cartridge hub 13.

Figure 14:
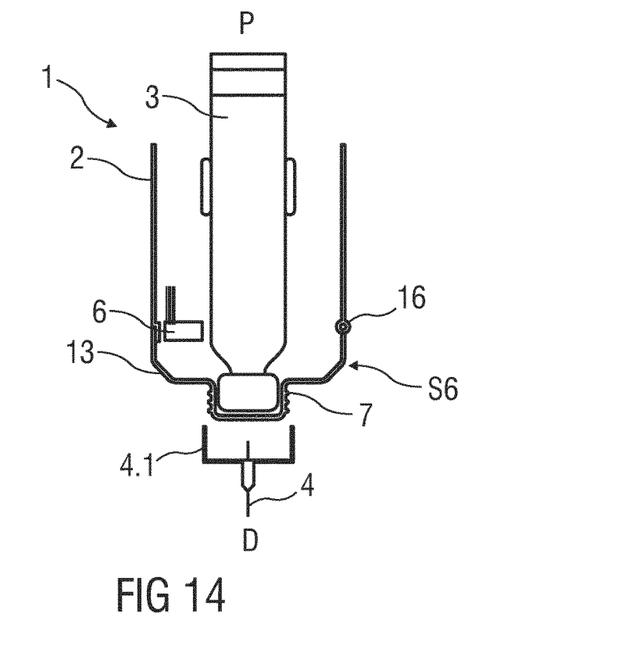
FIG. 14 is a schematic longitudinal section of a sixth exemplary embodiment of the drug delivery device, wherein a hinge is arranged between the body and the cartridge hub and the cartridge hub is rotated about the hinge for closing the body.
Figure 15:
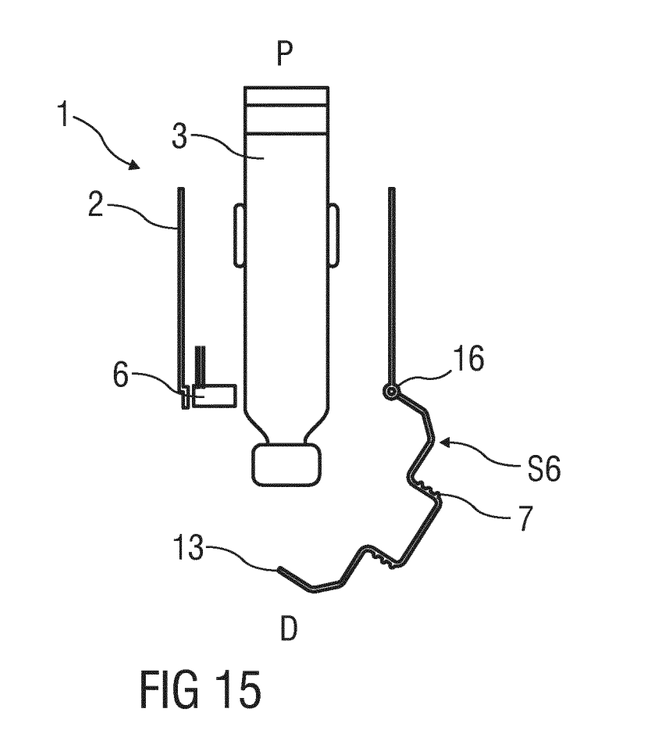
FIG. 15 is a schematic longitudinal section of the sixth exemplary embodiment of the drug delivery device, wherein the cartridge hub is rotated about the hinge for exposing the port.

A sixth embodiment is illustrated in FIG. 14. This embodiment is extension of the fifth embodiment. The port 6 is located within the body 2 next to the cartridge 3 behind a cartridge hub 13 comprised in the safety mechanism S6. The cartridge hub 13 comprises the threaded area 7, to which the needle 4 can be attached. The cartridge hub 13 is adapted to be attached to the body 2 as in FIG. 14. In the sixth embodiment a hinge 16 is provided on the body 2 for hinging the cartridge hub 13 to the body 2 to prevent it from detaching completely from the body 2. In the state shown in FIG. 14 the port 6 is hidden behind the cartridge hub 13 and cannot be accessed by the user. In order to access the port 6 the needle 4 is removed from the drug delivery device 1, and then the cartridge hub 13 is rotated about the hinge 16 as illustrated in FIG. 15. This allows access to the port 6 for the user, but prevents them from fitting a needle 4 to the cartridge 3 as the cartridge 3 is not threaded. The user could likewise rotate the cartridge hub 13 for opening the body 2 while the needle 4 is still attached to the cartridge hub 13.

Instead of the threaded area 7 the adapter 7 may comprise other means for attaching the needle 4 such as a bayonet fit, a cone or a Luer-lock.

The safety mechanism may in general comprise either purely mechanical means or an electronically actuated mechanical system. The safety mechanism could potentially make use of physical detents or magnetic elements to assist in the latching of the parts into the open or closed positions.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-litho-cholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. Drug delivery device for administering a drug, comprising:
   a body adapted to retain a cartridge containing a drug,
   at least one electrical unit (EU) and a port for electrically contacting the electrical unit (EU),
   an adapter for attaching an injection needle to the drug delivery device,
   wherein the body is attached to the drug delivery device during dose delivery and comprises a safety mechanism arranged to prevent access to the port whilst an injection needle is in fluid communication with the cartridge and arranged to prevent establishing a fluid communication between the injection needle and the cartridge whilst the port is accessible, wherein the safety mechanism of the body is arranged to cover the adapter when the port is accessible or to move at least part of the body to a position relative to the cartridge such that the at least part of the body prevents establishing fluid communication between the injection needle and the cartridge.

2. Drug delivery device according to claim 1, wherein the body comprises an inner body slidable within an outer body between a proximal position (PP) and a distal position (DP), wherein the inner body and the outer body are attached to the drug delivery device during dose delivery, wherein the adapter is arranged on the inner body, and wherein the cartridge and the port are fixed to the outer body, wherein a first opening is provided in the outer body for accessing the port, wherein a sliding cover is fixed to the inner body such that the cover closes the first opening when the inner body is in the proximal position (PP) and that the cover reveals the first opening when the inner body is in the distal position (DP).

3. Drug delivery device according to claim 2, wherein a slide handle is coupled to the cover.

4. Drug delivery device according to claim 1, wherein the body comprises an inner body slidable within an outer body between a proximal position (PP) and a distal position (DP), wherein the inner body and the outer body are attached to the drug delivery device during dose delivery, wherein the adapter is arranged on the inner body and extendible through a second opening in the outer body, and wherein the cartridge and the port are fixed to the inner body, wherein a first opening is provided in the inner body for accessing the port, wherein a sliding cover is fixed to the outer body such that the sliding cover closes the first opening when the inner body is in the distal position (DP) and that the sliding cover reveals the first opening when the inner body is in the proximal position (PP).

5. Drug delivery device according to claim 4, wherein a diameter of the second opening is smaller than a diameter of a needle hub of the needle for attaching the needle to the adapter.

6. Drug delivery device according to claim 1, wherein the port and the adapter are located on a distal end of the drug delivery device and accessible through respective first and second openings in a distal face of the body, wherein a sliding cover is movable in the distal face such that it either covers the first opening or the second opening.

7. Drug delivery device according to claim 6, wherein a cartridge holder is arranged within the body for retaining the cartridge, wherein the adapter is arranged on the cartridge holder.

8. Drug delivery device according to claim 6, wherein the cartridge and/or the cartridge holder is/are slidably arranged within the body between a proximal position (PP), in which the adapter is inside the body, and a distal position (DP), in which the adapter extends beyond the distal face.

9. Drug delivery device according to claim 8, wherein a drive is arranged for moving the cartridge and/or the cartridge holder towards the distal position (DP).

10. Drug delivery device according to claim 9, wherein the drive comprises at least one spring.

11. Drug delivery device according to claim 9, wherein the drive comprises an electro mechanical drive.

12. Drug delivery device according to claim 9, wherein the drive comprises a mechanical link connecting the motion of the cover to the motion of the cartridge and/or cartridge holder.

13. Drug delivery device according to claim 1, wherein the adapter comprises a threaded area for attaching a threaded needle.

14. Drug delivery device for administering a drug, comprising:
- a body adapted to retain a cartridge containing a drug,
- at least one electrical unit (EU) and a port for electrically contacting the electrical unit (EU),
- an adapter for attaching an injection needle to the drug delivery device,
- a safety mechanism arranged to prevent access to the port whilst an injection needle is in fluid communication with the cartridge and/or arranged to prevent establishing a fluid communication between an injection needle and the cartridge whilst the port is accessible, wherein the port is located within the body, wherein a cartridge hub is adapted to be attached to the body during dose delivery so as to close a distal end of the body thereby covering the port during dose delivery, wherein the adapter is arranged on the cartridge hub, and wherein the cartridge hub is adapted to be detached from at least part of the body so as to uncover the port.

15. Drug delivery device according to claim 14, wherein a hinge is provided on the body for hinging the cartridge hub to the body such that the cartridge hub is rotatable about the hinge for opening or closing the distal end of the body.

* * * * *